(12) United States Patent
Utsui

(10) Patent No.: US 6,482,150 B2
(45) Date of Patent: Nov. 19, 2002

(54) OPTICAL SYSTEM FOR THE LIGHT SOURCE DEVICE OF A VIDEO ENDOSCOPE SYSTEM

(75) Inventor: Tetsuya Utsui, Saitama-ken (JP)

(73) Assignee: Asahi Kogaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/908,700

(22) Filed: Jul. 20, 2001

(65) Prior Publication Data
US 2002/0022768 A1 Feb. 21, 2002

(30) Foreign Application Priority Data
Jul. 27, 2000 (JP) .......................................... 2000-227328

(51) Int. Cl.[7] ................................................ A61B 1/06
(52) U.S. Cl. ...................................... 600/178; 600/181
(58) Field of Search ................................ 600/178, 180, 600/181; 348/68, 70; 362/574

(56) References Cited

U.S. PATENT DOCUMENTS 4,974,076 A * 11/1990 Nakamura et al. ............. 348/71
6,161,035 A    12/2000 Furusawa

FOREIGN PATENT DOCUMENTS

WO         99/37204         7/1999

* cited by examiner

Primary Examiner—John Mulcahy
(74) Attorney, Agent, or Firm—Greenblum & Bernstein, P.L.C.

(57) ABSTRACT

An video endoscope system has, as main components, a video endoscope equipped with a light guide, a light source device for supplying illumination light and exciting light to the light guide, and an endoscope processor to process image signals and to control the light source device. The light source device is composed of a white light source for generating a collimated beam of white light, an ultraviolet light source for generating a collimated light beam having wavelengths in the ultraviolet region, and a UV reflection filter for transmitting white light while reflecting ultraviolet light, as main components. In the optical system for the light source device, the UV reflection filter is arranged at an angle of 45 degrees to both the collimated beam of white light and the collimated light beam having wavelengths in the ultraviolet region that intersect each other orthogonally.

8 Claims, 9 Drawing Sheets

UV reflection filter (incident angle = 45°)

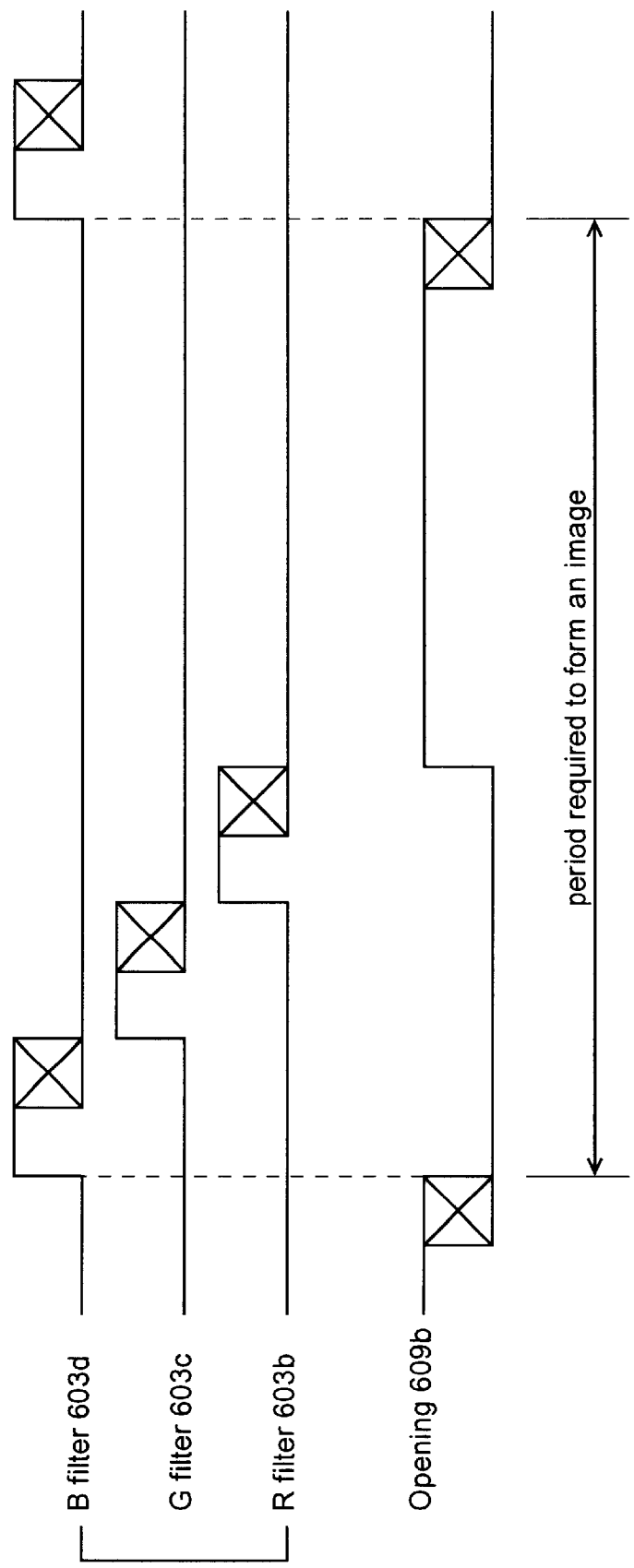

OPTICAL SYSTEM FOR THE LIGHT SOURCE DEVICE OF A VIDEO ENDOSCOPE SYSTEM

BACKGROUND OF THE INVENTION

1. Field of the Invention

The present invention relates to a video endoscope system used in medical applications to obtain images of a surface of a subject illuminated by visible light and images of the subject through autofluorescence resulting from excitation light and specifically relates to an optical system for the light source device that generates illuminating light and excitation light to supply them into the video endoscope. The present disclosure relates to subject matter contained in Japanese Patent Application No. 2000-227328 (filed on Jul. 27, 2000), which is expressly incorporated herein by reference in its entirety.

2. Description of the Related Art

In recent years, a method has been proposed for observing the autofluorescence of a subject (specifically, body cavity wall) with a video endoscope systems. In a body cavity wall irradiated by light of a specific wavelength (generally ultraviolet light), the tissues are excited to emit fluorescence. The intensity of the fluorescence generated by healthy tissue is stronger than that generated from unhealthy tissue, such as cancerous tissue. This causes an intensity distribution of autofluorescence in the body cavity when the cavity includes unhealthy tissue. capturing images of autofluorescence from the body cavity wall with the solid state image sensing device (CCD) of the video endoscope makes it possible to observe special images of the body cavity wall that differ from images of the body cavity wall obtained by normal illumination with visible light.

As such video endoscope systems that allow the fluorescence observation, a video endoscope system of the so-called RGB frame sequential system is used, which has an RGB rotating shutter for separating white light (visible light) emitted from a light source into red, green, and blue light components, an illumination optical system for transmitting in sequence the red, green and blue light to the proximal end of the video endoscope and an ultraviolet source for supplying ultraviolet light to excite the body cavity wall into the above-mentioned illumination optical system. FIG. 7 shows an optical configuration in the light source device 60 of such a video endoscope system. FIG. 8 is a front view of an RGB rotating shutter 603 and a UV rotating shutter 609 in the light source device 60.

As shown in FIG. 7, the light source device 60 is composed of a white light source 601, an infrared cut-off filter 602, the RGB rotating shutter 603, a UV reflection filter 604, a light aperture diaphragm 605, a condenser lens 606, an ultraviolet light source 607, a UV transmission filter 608, the UV rotating shutter 609, and a mirror 610.

The RGB rotating shutter 603 is, as shown in FIG.7 and FIG. 8A, a disc coaxially mounted on a drive shaft of a motor 603a, on which are formed three fan-shaped window, respectively fitted with red, green and blue filters 603b–603d. These filters 603b–603d are band pass filters, respectively transmitting red, green and blue light and arranged side by side at predetermined intervals on the same circle coaxial with outer edge of the disc. These filters 603b–603d are arranged to occupy almost a semicircular area within this circle.

As shown in FIG. 7 and FIG. 8, UV rotating shutter 609 is a disk coaxially mounted on a drive shaft of a motor 609a, on which are formed a fan-shaped opening whose apex coincides with the center of the disc. The central angle of the opening 609b is slightly less than 180 degrees.

As shown in FIG. 7, the collimated beam of white light emitted from the white light source 601 is deprived of its wavelength components in the infrared region by the infrared cut-off filter 602, transmitted through one of the red, green or blue filters 603b–603d provided on the RGB rotating shutter 603 and the UV reflection filter 604, and subsequently adjusted to have a proper amount of light by the light aperture diaphragm 605, and focused onto a proximal end face 70a of a light guide 70 of the video endoscope by the condenser lens 606.

The collimated light beam consisting of wavelengths in the ultraviolet region emitted from the ultraviolet light source 607 in a direction parallel to the collimated beam of white light is filtered by the UV transmission filter 608 to be a collimated beam having wavelengths only in the ultraviolet region, then transmitted through the opening 609b formed on the UV rotating shutter 609, then sequentially reflected by the mirror 610 and the UV reflection filter 604 to shift to trace the same optical path as the above-emitted collimated beam of white light, subsequently adjusted to have a proper amount of light by the light aperture diaphragm 605, and focused onto the proximal end face 70a of the light guide 70 by the condenser lens 606.

The RGB rotating shutter 603 and the UV rotating shutter 609 are rotated by the motors 603a and 609a, respectively, whose speeds and rotation phases are controlled, so that a beam consisting of a blue component (blue light), a beam consisting of a green component (green light), a beam consisting of a red component (red light), and a beam having wavelengths in the ultraviolet region (ultraviolet light) are incident onto the proximal end face of the light guide 70, in turn. FIG. 9 gives a schematic representation of these respective beams incident on the condenser lens 606. In FIG. 9, an interval designated by two broken lines indicates a period in which the rotating shutter 603 and the rotating shutter 609 round in synchronism with each other, with periods corresponding to protruding portions of the lines in the graph indicating periods in which the collimated beam of white light enters one of RGB filters 603b–603d or a period in which a collimated light beam consisting of the wavelengths in the ultraviolet region streams into the opening 609b, respectively. A symbol "x" appearing on each line indicates a blank period in which no beam enters the condenser lens 606.

As shown in FIG. 9, while the rotating filter 603 and the rotating shutter 609 round, blue light, green light, red light, and ultraviolet light are sequentially onto the condenser lens 606. Here, since the fan-shaped opening 609b formed on the UV rotating shutter 609 has a larger center angle than the center angles of each of the three fan-shaped windows formed on RGB rotating shutter 603, the period when ultraviolet light is incident on the condenser lens 606 is longer than any one of periods for blue light, green light and red light.

Light of each color that enters the light guide 70 from the proximal end face 70a thereof is transmitted through this light guide 70 to its distal end face to illuminate or irradiate the body cavity wall through a light distribution lens fitted onto the distal end of the video endoscope (not shown in the figure). Images of the body cavity wall illuminated sequentially by the blue light, the green light, and the red light which are formed by an objective optical system (not shown in the figure), and an image of autofluorescence of the body cavity wall that is excited by the ultraviolet light which is formed by the objective optical system (not shown in the figure) are sequentially picked up by the CCD installed in the video endoscope, converted into electronic signals, and sent to an image signal processing circuit within an endoscope processor (not shown in the figure).

In the optical system of the above-mentioned light equipment 60, the two light sources 601, 607 are arranged side by side so that a collimated beam of white light and a collimated beam consisting of wavelengths in the ultraviolet region are parallel to each other. These two collimated light beams are guided to a common optical path through the mirror 610 and the UV reflection filter 604. Thus, these two beams share light aperture diaphragm 605 and condenser lens 606.

However, a configuration in which two collimated light beams emitted from two light sources 601, 607 are arranged in parallel needs a large total number of optical elements. This leads to increased mass and bulk of the optical system and the whole light source device as well. Additionally, the fact that several optical elements such as mirrors are used to reflect the beam multiple times requires an excessive amount of time to adjust optical axes of the optical system.

Moreover, UV reflection filter 604 shown in FIG. 7 is required to transmit the beam of white light efficiently, and to reflect the beam consisting of wavelengths in the ultraviolet region efficiently, otherwise, light sufficient to illuminate or excite the subject (the body cavity wall) cannot be introduced into light guide 70.

SUMMARY OF THE INVENTION

It is the main object of the present invention to provide an optical system for a light source device for a a video endoscope system that can meet the purpose of the device, but with fewer optical elements, and that enables an operator to adjust optical axes easily and relatively quickly, without consuming excessive time. An additional object of the present invention is to provide a optical system for a light source device such that a UV reflection filter allows a beam of white light to pass therethrough efficiently, while also reflecting a beam consisting of wavelengths in the ultraviolet region efficiently.

The optical system according to present invention devised to resolve the above-described problem has a condenser lens for converging a light beam onto a proximal end face of a light guide, a visible light source that emits a first collimated light beam having wavelengths in a visible region and is arranged so that the first collimated light beam is incident on the condenser lens, an ultraviolet light source that emits a second collimated light beam having wavelengths in an ultraviolet region and is arranged so that the second collimated light beam intersects the first collimated light beam orthgonally, and a UV reflection filter arranged at a position where the first collimated light beam and the second collimated light beam intersect. The UV reflection filter is inclined to each collimated light beam at an angle of 45 degrees, transmits the first collimated light beam, and reflects the second collimated light beam toward the condenser lens.

By this arrangement, the first collimated light beam that was emitted from the visible light source and has wavelengths in the visible region is transmitted through the UV reflection filter to enter the condenser lens, and the second collimated light beam having wavelengths in the ultraviolet region is reflected by the UV reflection filter by 90 degrees to enter the condenser lens. Thus, the second collimated light beam having wavelengths in the ultraviolet region is reflected only once to enter the condenser lens, so that the number of the optical elements can be reduced. As a result, the adjustment of the optical axes can be done easily.

Because the UV reflection filter is inclined to both collimated light beams at an angle of 45 degrees, the UV reflection filter transmits the first collimated light beam having wavelengths in the visible region, while efficiently reflecting the second collimated light beam consisting of wavelengths in the ultraviolet region. This configuration of the optical system makes it possible to introduce sufficient amount of light to illuminate or excite the subject (the body cavity wall) into the light guide.

The invention will be described below in detail with reference to the accompanying drawings, in which:

FIG. 1 is a schematic illustration showing an internal structure of the video endoscope system which is an embodiment of the light source device according to the present invention;

FIG. 2 is an illustration showing an optical configuration of the light source device;

FIG. 3A is a front view of an RGB rotating shutter of the light source device and FIG. 3B a front view of a UV rotating shutter;

FIG. 4 is a block diagram showing a circuit of the endoscope processor;

FIG. 5 is an illustration concretely showing the arrangement of the UV reflection filter, an infrared cut-off filter, and the UV transmission filter;

FIG. 6 is a graph showing the spectral reflectance characteristics of the UV reflection filter at the condition the beam enters the plane of the UV reflection filter at an incident angle of 45 degrees;

FIG. 7 is an illustration showing an optical configuration of the light source device in a conventional video endoscope system;

FIG. 8A is a front view of an RGB rotating shutter in the conventional light source device and FIG. 8B is a front view of the UV rotating shutter; and FIG. 9 is a timing chart showing transmission phases for beams of respective wavelengths incident on the condenser lens in the conventional light source device.

BRIEF DESCRIPTION OF THE SEVERAL VIEWS OF THE DRAWING

An embodiment of a light source device according to the present invention will be described, with reference to the drawings.

Figure 1:
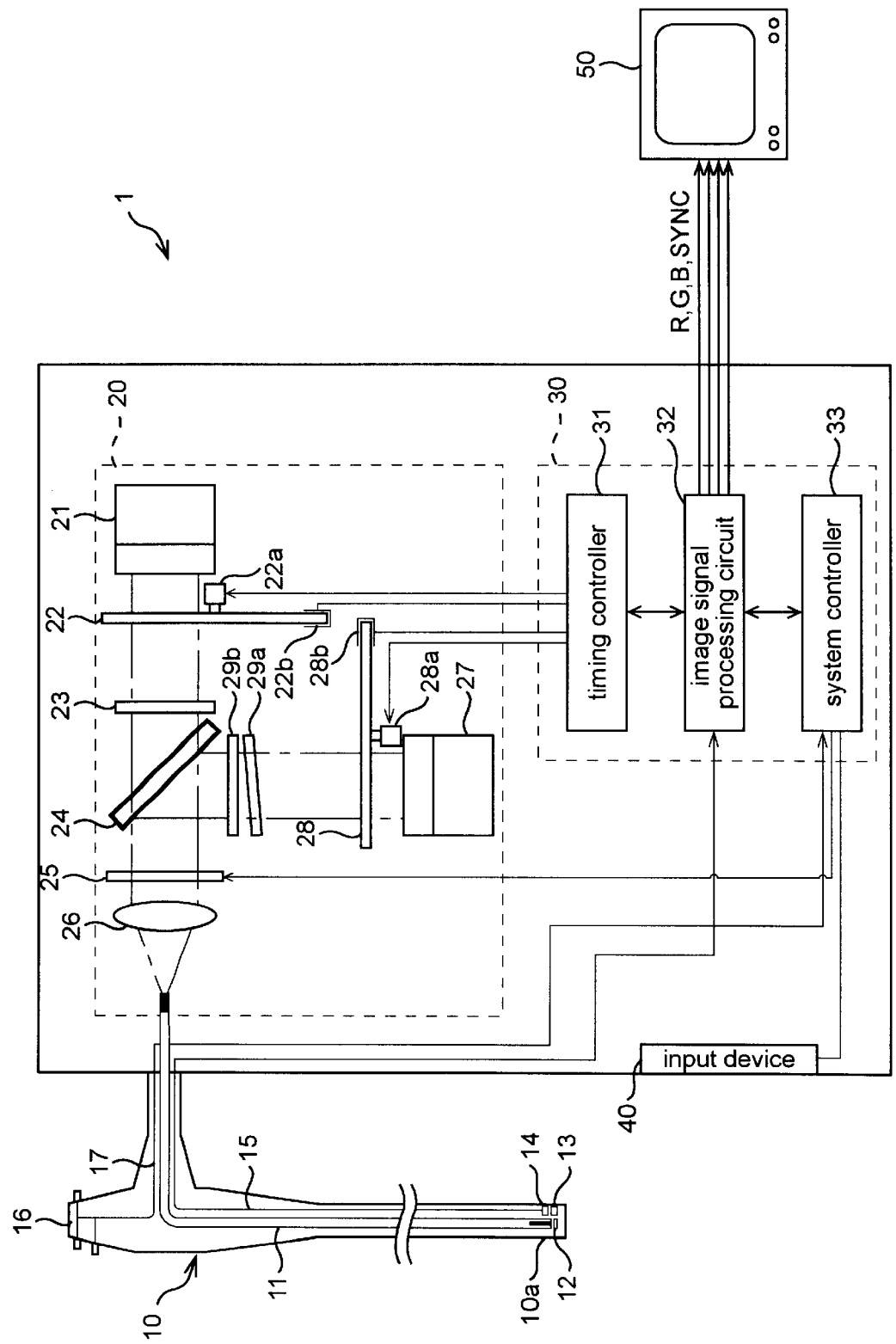
FIG. 1 is a schematic illustration showing an electronic endoscope system 1 which is one embodiment of the light source device according to the present invention.

This video endoscope system 1 consists of a video endoscope 10 that is to be inserted into the body cavity of the patient from its distal end 10a, a light source device to supply illumination light and exciting light to the video endoscope 10, an endoscope processor 30 to control this light source device 20 and to receive and process image signals from the video endoscope 10, and an input device 40 equipped with various operation buttons and switches. Among these components, the light source device 20, the endoscope processor 30, and the input device 40 are housed in a common casing.

The endoscope processor 30 has a timing controller 31 for synchronizing the illuminating light, the excitation light, and the image signals, an image signal processing circuit 32 to process the image signals from the video endoscope 10 in order to convert them into RGB image signals to send them to a monitor 50, and a system controller 33 to control the whole system 1 in accordance with instructions entered from the input device 40.

The video endoscope 10 has a light guide fiber bundle (hereinafter abbreviated as a "light guide") 11 connected to light source device 20, a light distribution lens 12 for wide distribution of the illumination light and the exciting light transmitted through the light guide 11, an objective optical system 13 to form an image of the subject (body cavity wall), a solid state image sensing device (CCD) 14 arranged in the vicinity of an imaging plane of the objective optical system 13 to pick up an image of the body cavity wall, a signal cable 15 through which transfer pulses to drive this CCD 14 are sent, and through which image signals are sent to an image signal processing circuit 32, a bending mechanism for bending the distal end 10a and its vicinity (not shown in the figure), an operating section 16 equipped with several buttons, switches and a dial for manipulating the bending mechanism (not shown), and signal cable 17 through which various signals are transmitted from operating section 16 to the system controller 33.

Figure 2:
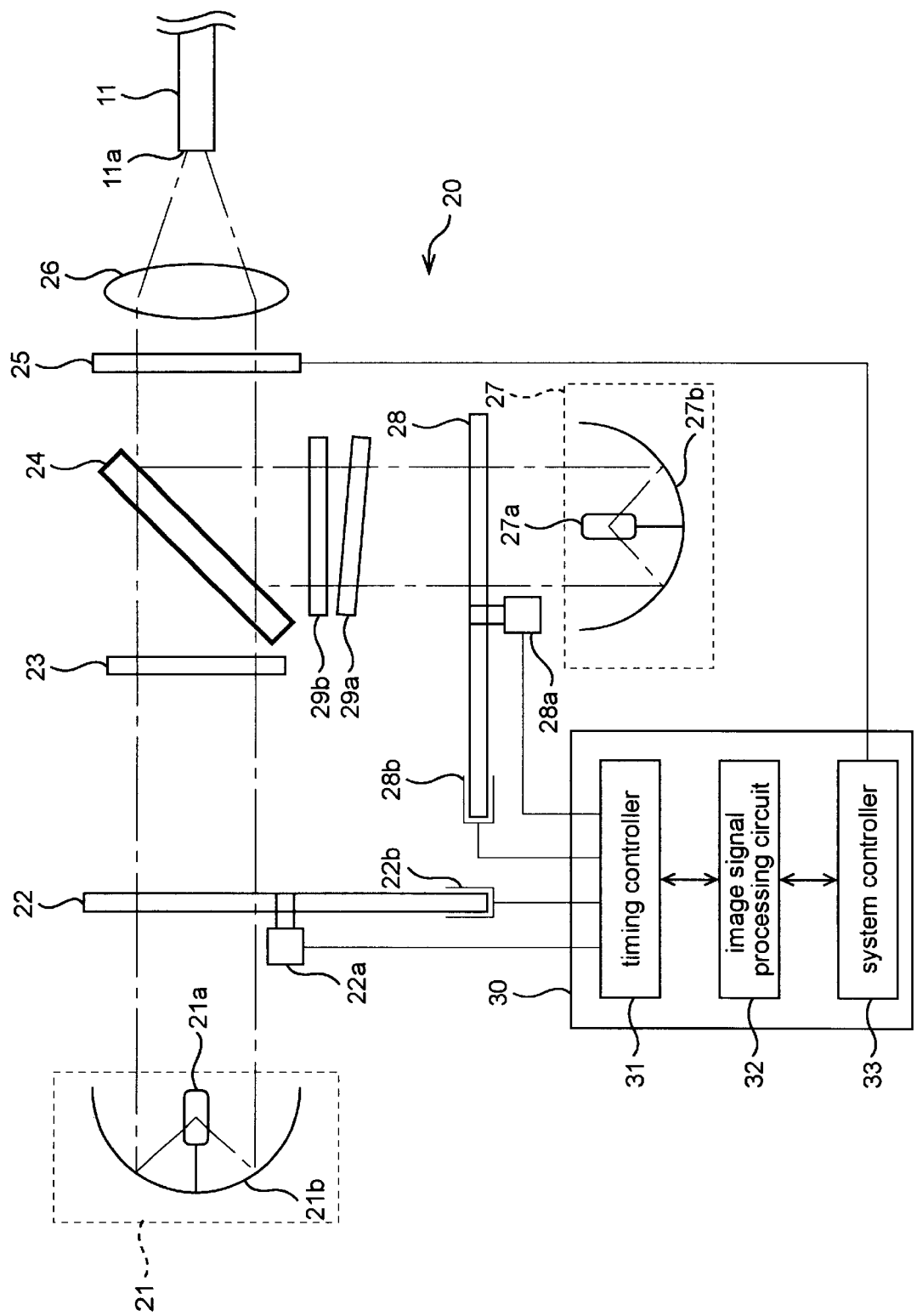

FIG. 2 is a drawing showing an optical configuration of the light equipment 20. As shown in FIG. 1 and FIG. 2, the light source device 20 is composed of a white light source 21, an RGB rotating shutter 22, an infrared cut-off filter 23, a UV reflection filter 24, a light aperture diaphragm 25, a condenser lens 26, an ultraviolet light source 27, a UV rotating shutter 28, and two UV transmission filters 29a, 29b.

The white light source 21 has a xenon lamp 21a for emitting white light as illumination light for normal observations and a reflector 21b for reflecting the white light emitted from the xenon lamp 21a as a collimated light beam in its interior. The ultraviolet light source 27 has an ultraviolet lamp 27a for emitting ultraviolet light that excites the subject (body cavity wall) to generate autofluorescence, and a reflector 27b to reflect the ultraviolet light emitted from the ultraviolet lamp 27a as a collimated light beam in its interior. The white light source 21 and the ultraviolet light source 27 are arranged so that the direction in which white light source 21 emits the collimated white light beam and the direction in which the ultraviolet light source 27 emits the collimated ultraviolet light beam lie at right angles to each other.

The collimated beam of white light emitted from the white light source 21 (hereinafter, referred to as "collimated white light beam") is transmitted through the RGB rotating shutter 22 described later, with wavelength components in the infrared region to be removed by the infrared cut-off filter 23, and transmitted through the UV reflection filter 24 (described further below). Subsequently, the collimated white light beam is adjusted so as to have proper beam diameter by the light aperture diaphragm 25 and focused onto the proximal end face 11a of the light guide 11 by the condenser lens 26.

On the other hand, the collimated light beam consisting of wavelengths in the ultraviolet region emitted from ultraviolet light source 27 (hereinafter, referred to as "collimated ultraviolet light beam"), crossing at right angles to the collimated white light beam, is transmitted through the UV rotating shutter 28 (described further below), filtered so as to consist of only wavelength components in the ultraviolet region by the UV transmission filters 29a, 29b, and reflected by UV reflection filter 24 (described further below). Subsequently, the collimated ultraviolet light beam is adjusted so as to have the proper beam diameter by the light aperture diaphragm 25, and focused onto the proximal end face 11a of the light guide 11 by the condenser lens 26.

Figure 3B:
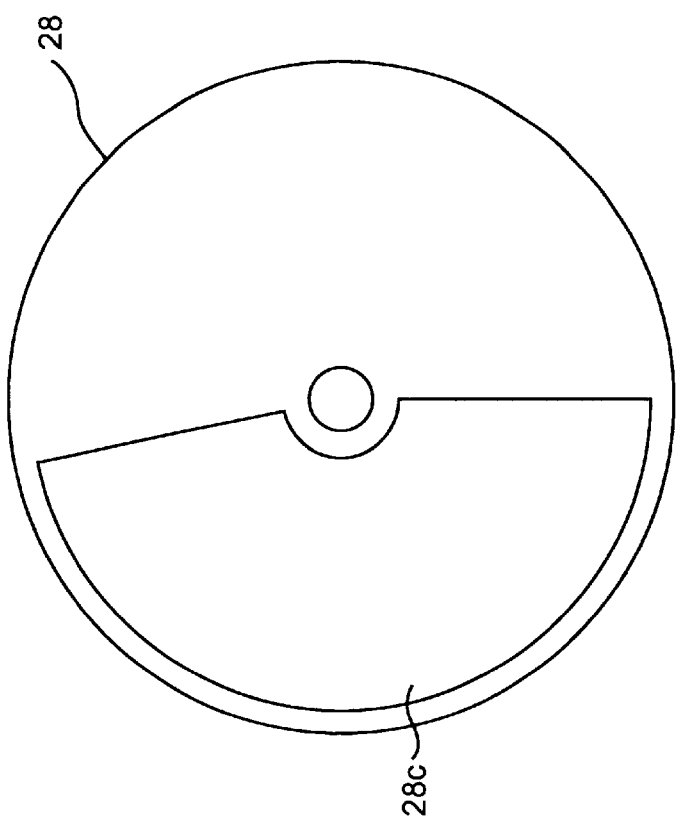
Figure 3A:
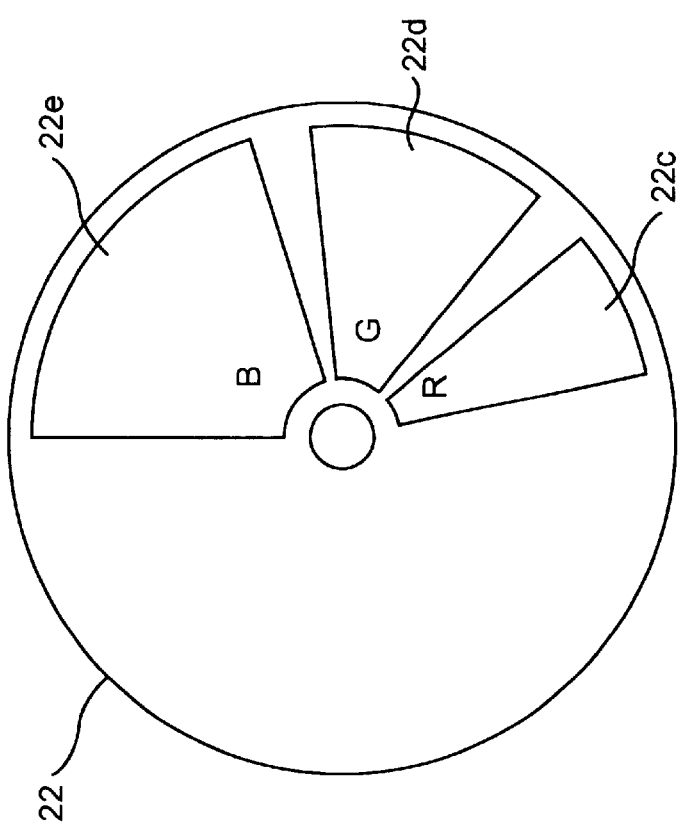

FIG. 3A is a front view of the RGB rotating shutter 22, while FIG. 3B is a front view of the UV rotating shutter 28. As shown in FIG. 1 through FIG. 3, RGB rotating shutter 22 is a disc coaxially mounted on a drive shaft of a motor 22a, on which three fan-shaped windows are formed. Apexes of each fan-shaped window coincides with the center of the disc. Red, green and blue filters 22c–22e are fitted in the fan-shaped windows, respectively. These red, green and blue filters 22c–22e are band-pass filters, respectively transmitting light of only one wavelength region among red (R), green (G), and blue (B) regions. They are arranged side by side at predetermined intervals on the same circle, whose center coincides with the center of the disc. These red, green and blue filters 22c–22e are arranged so as to occupy almost a semicircular portion of the same circumference. When this RGB rotating shutter 22 is rotated by the motor 22a, the red, green and blue filters 22c–22e are repeatedly brought into the optical path of the collimated white light beam emitted from the white light source 21 in the sequence of R-G-B. As a result, the collimated white light beam is sequentially converted into a beam consisting of only light in the red wavelength region (red light), a beam consisting of only light in the green wavelength region (green light), and a beam consisting of only light in the blue wavelength region (blue light). The red, green and blue light is transmitted through the UV reflection filter 24, and then focused on the proximal end face 11a of the light guide 11 by the condenser lens 26 in the repetitive sequence.

As shown in FIG. 1 through FIG. 3, the UV rotating shutter 28 is a disc coaxially mounted on a drive shaft of a motor 28a, on which a fan-shaped opening 28c are formed. Apex of the fan-shaped opening 28c coincides with the center of the disc. The central angle subtended by the arc of the opening 28c is slightly smaller than 180 degrees. When this UV rotating shutter 28 is rotated by the motor 28a, the opening 28c is repeatedly inserted in the optical path of the collimated ultraviolet light beam emitted from the ultraviolet light source 27. As a result, the collimated ultraviolet light beam is entered into the UV reflection filter 24 intermittently to be reflected, and then focused on the proximal end face 11a of the light guide 11 by the condenser lens 26.

As shown in FIG. 1 and FIG. 2, sensors 22b and 28b are respectively allocated by outer edges of the RGB rotating shutter 22 and the UV rotating shutter 28 to detect the rotation condition of the shutters 22 and 28. The sensors 22 and 28 are respectively connected to a timing controller 31 as a controller to give the information concerning the rotation of the shutters 22 and 28 to a rotating shutter control circuit 312 (FIG. 4) that is a part of the timing controller 31. Motors 22a and 28a are connected to the rotation shutter control circuit 312, and the speeds and phases of the rotation of the motors 22a and 28a are controlled by the rotation shutter control circuit 312 so that the red light, green light, blue light, and ultraviolet light focused by the condenser lens 26 are incident on the proximal end face 11a of the light guide 11 in sequence.

The light aperture diaphragm 25 is electrically connected to a light aperture diaphragm control circuit 333 (FIG. 4) in the system controller 33 in the endoscope processor 30, so that amount of light of each of the red, green, blue, and ultraviolet light entering the condenser lens 26 is adjusted by the light aperture diaphragm 25 which is controlled by the system controller 33.

Figure 4:
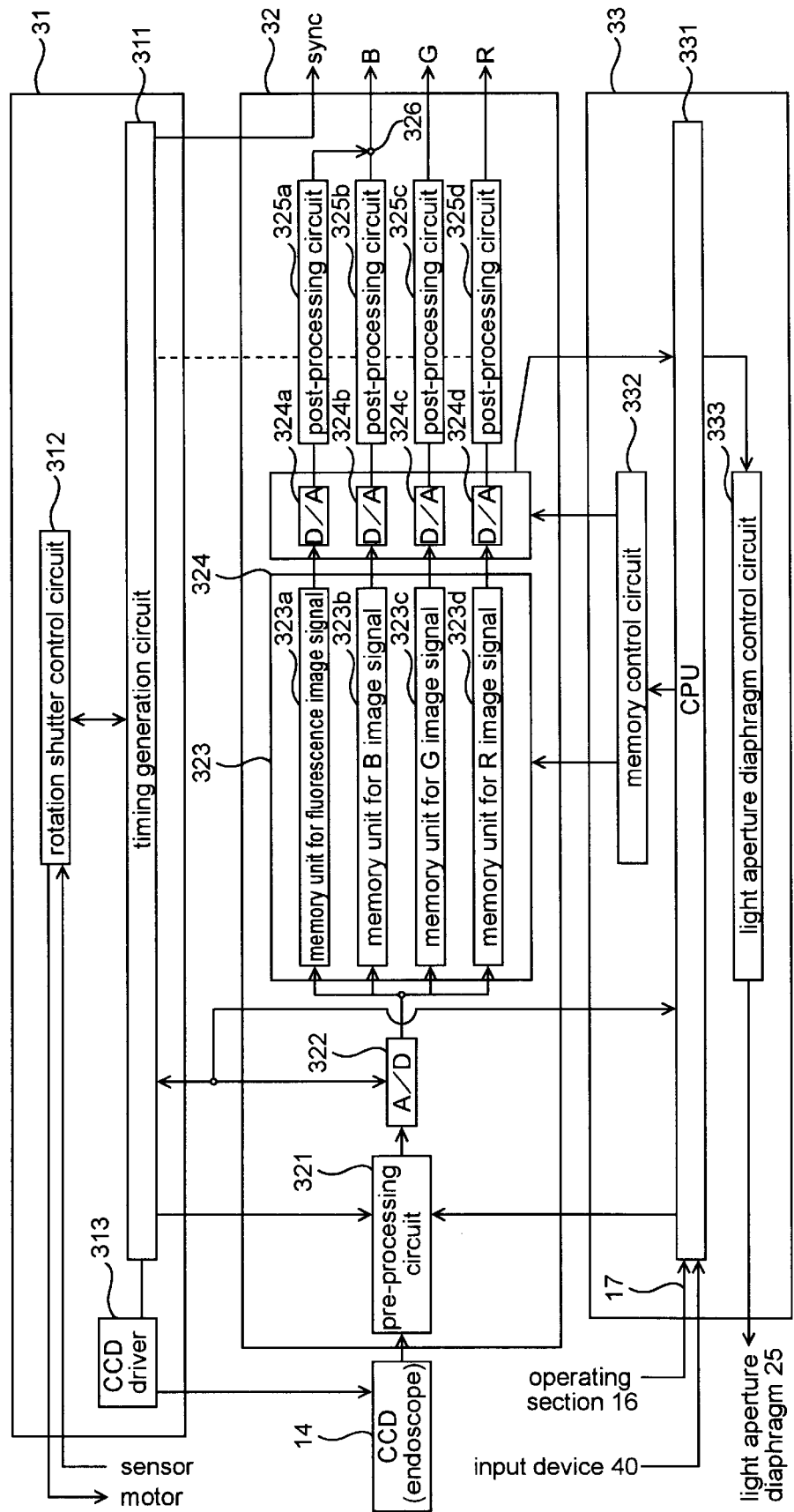

FIG. 4 is a block diagram showing the internal configuration of the endoscope processor 30. As shown in this FIG. 4, timing controller 31 includes a timing generation circuit 311, the rotating shutter control circuit 312 and a CCD driver 313. The timing generation circuit 311 generates synchronization pulse signals to synchronizes the illuminating light, the excitation light, and image signals with one another. The rotating shutter control circuit 312 controls the motors 22a and 28a that rotatively drive the RGB rotating shutter 22 and the UV rotating shutter respectively, according to the rotation conditions detected by the sensors 22b and 28b. The CCD driver 313 sends a transfer pulse to the CCD 14 in response to the synchronization pulse signal received from the timing generation circuit 311.

Image signal processing circuit 32 is composed of a pre-processing circuit 321, an analog/digital (A/D) converter 322, a memory part 323, a digital/analog (D/A) converter section 324, post-processing circuits 325a–325d, and an adder 326. Memory section 323 is composed of memory unit 323a for the fluorescence image signal, memory unit 323b for the B image signal, memory unit 323c for the G image signal, and memory unit 323d for the R image signal. D/A converter section 324 comprises D/A converters 324a–324d corresponding to the memory units 323a–323d, respectively.

The system controller 33 comprises a CPU 331, a memory control circuit 332 and the light aperture diaphragm control circuit 333. The CPU 331 is connected to the input device 40 and to the operating section 16 of the video endoscope 10 via electric wire 17, which is a central processing circuit for controlling the whole of system 1 according to instructions entered from the input device 40 and the operating section 16. The memory control circuit 332 controls the memory units 323a–323d of the image signal processing circuit 32. The light aperture diaphragm control circuit 333 controls the aperture limits of the light aperture diaphragm 25 in response to image signals from the D/A converter section 324.

As described above, when red light, green light, blue light, and ultraviolet light are introduced in sequence into the light guide 11 through its proximal end face 11a, the subject (body cavity wall) is sequentially illuminated or irradiated by the red light, green light, blue light, and ultraviolet light transmitted in the light guide and emitted through its distal end face. The images of the body cavity wall illuminated with the red, green, and blue light and the image of the body cavity wall excited by the ultraviolet light to generate autofluorescence are sequentially formed on an imaging plane of CCD 14 by the objective optical system 13. The CCD 14 is driven by the CCD driver 313 receiving a synchronization pulse signal from the timing generation circuit 311 and sequentially reads the images of the subject formed from the illuminating light and the excitation light to convert them into electric signals (which are R image signal based on the red light, G image signal based on the green light, B image signal based on the blue light, and the fluorescence image signal based on the ultraviolet light).

Pre-processing circuit 321 receives the R image signal, the G image signal, the B image signal, and the fluorescence image signal, which are sequentially output from the CCD 14, and applies amplification, sample-and-hold, clamping, and gamma control processing to these image signals. Each of the image signals processed by the pre-processing circuit 321 is then converted into a digital signal by the A/D converter 322.

The R,G and B image signals and the fluorescence image signal sequentially converted into digital signals by the A/D converter 322 are distributed to the memory units 323a–323d, in accordance with to the respective signals from the memory control circuit 332 following instructions from the CPU 331. The R. G and B signals are temporarily stored in respective memory units 323a–323d, and then simultaneously output from the memory units 323a–323d, respectively. The digital signals output from the respective memory units 323a–323d are then respectively converted into analog signals by the corresponding D/A converters 324a–324d.

The R,G and B image signals and the fluorescence image signal that were converted into analog signals undergo processing of amplification, clamping, blanking, 75Ω driver, etc. by the respective post-processing circuits 325a–325d corresponding thereto.

Then, the B image signal to which the fluorescence image signal was added by the adder 326 is output to monitor 50 together with the G image signal and the R image signal. At the same time, a synchronization signal (SYNC) provided by the timing generation circuit 311 is also output to the monitor 50.

Compared with the R, G and B light reflected by the body cavity wall, the intensity of the autofluorescence emitted from the body cavity wall is extremely weak. To compensate the difference in intensity, the central angle of the fan-shaped opening 28c formed on the UV rotating shutter 28, as shown in FIG. 3, is larger than the central angles of each fan-shaped window formed on the RGB rotating filter 22. Accordingly, the duration for which the collimated ultraviolet light beam is transmitted through opening 28c and incident on the condenser lens 26 is longer than any period in which the collimated white light beam enters one of R, G and B filters 22c–22e and incident on the condenser lens 26 as one of the red light, the green light and the blue light. As a result, the image of the body cavity wall generating the autofluorescence formed by the objective optical system 13 accumulated in charge storages in the CCD 14, taking more time than those for images of the body cavity wall irradiated by the red light, the green light, or the blue light formed by the objective optical system 13. Thus, the fluorescence image signal is amplified to be signal levels close to that of each of the red, green and blue image signals. Incidentally, the fluorescence image signal may be further amplified by an amplifier circuit, as long as noise levels remain unnoticeable.

In the light source device 20 of the video endoscope system 1 explained above, UV reflection filter 24 is inclined at an angle of 45 degrees to the collimated visible light beams and to the collimated ultraviolet light beam, respectively, as described above. This arrangement is adopted for the following reasons.

Figure 5:
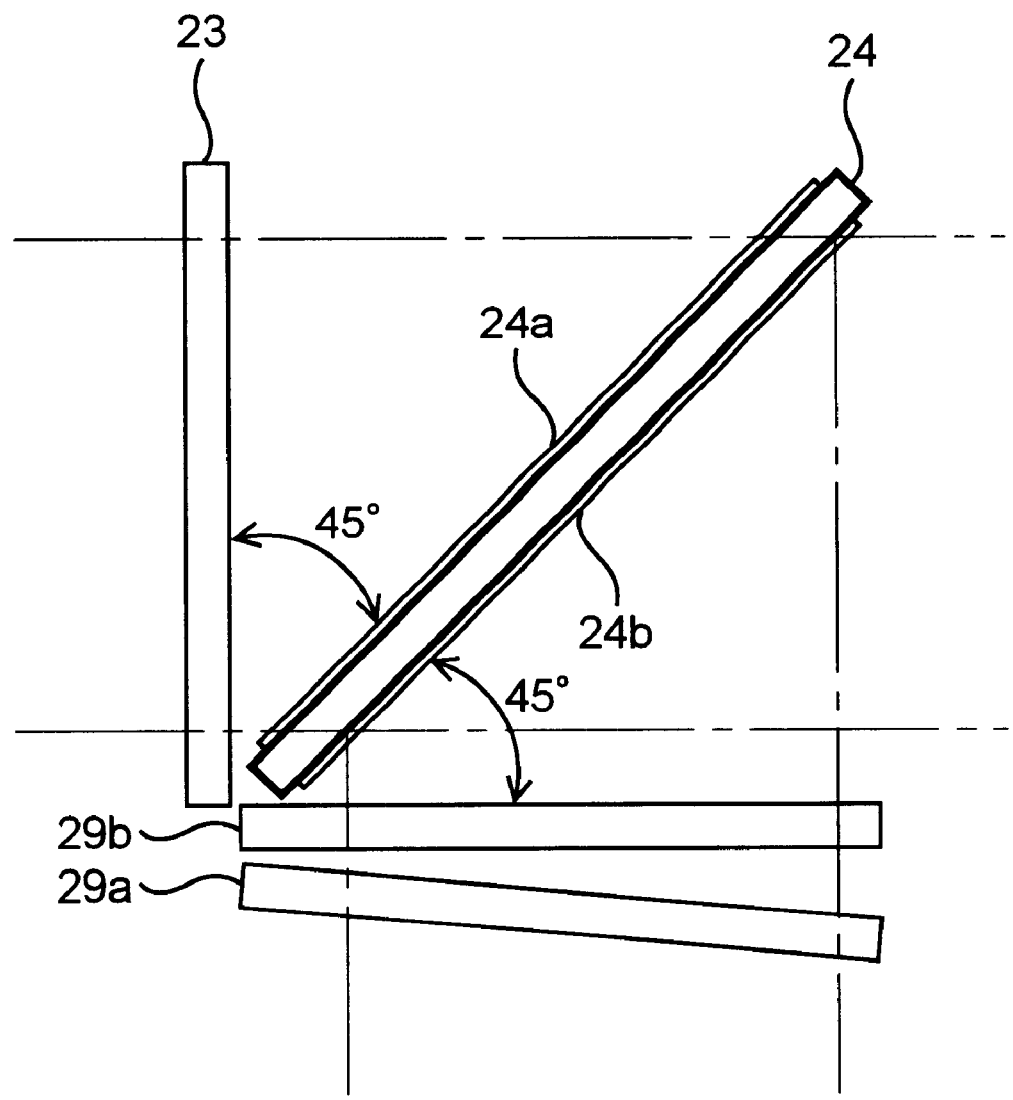
Figure 6:
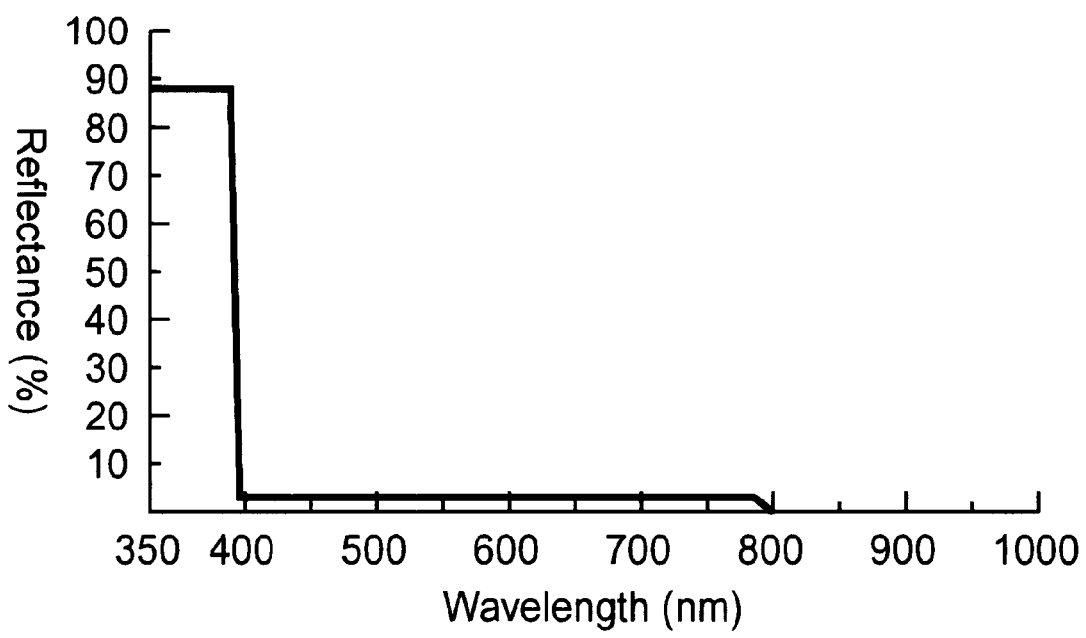
Figure 7:
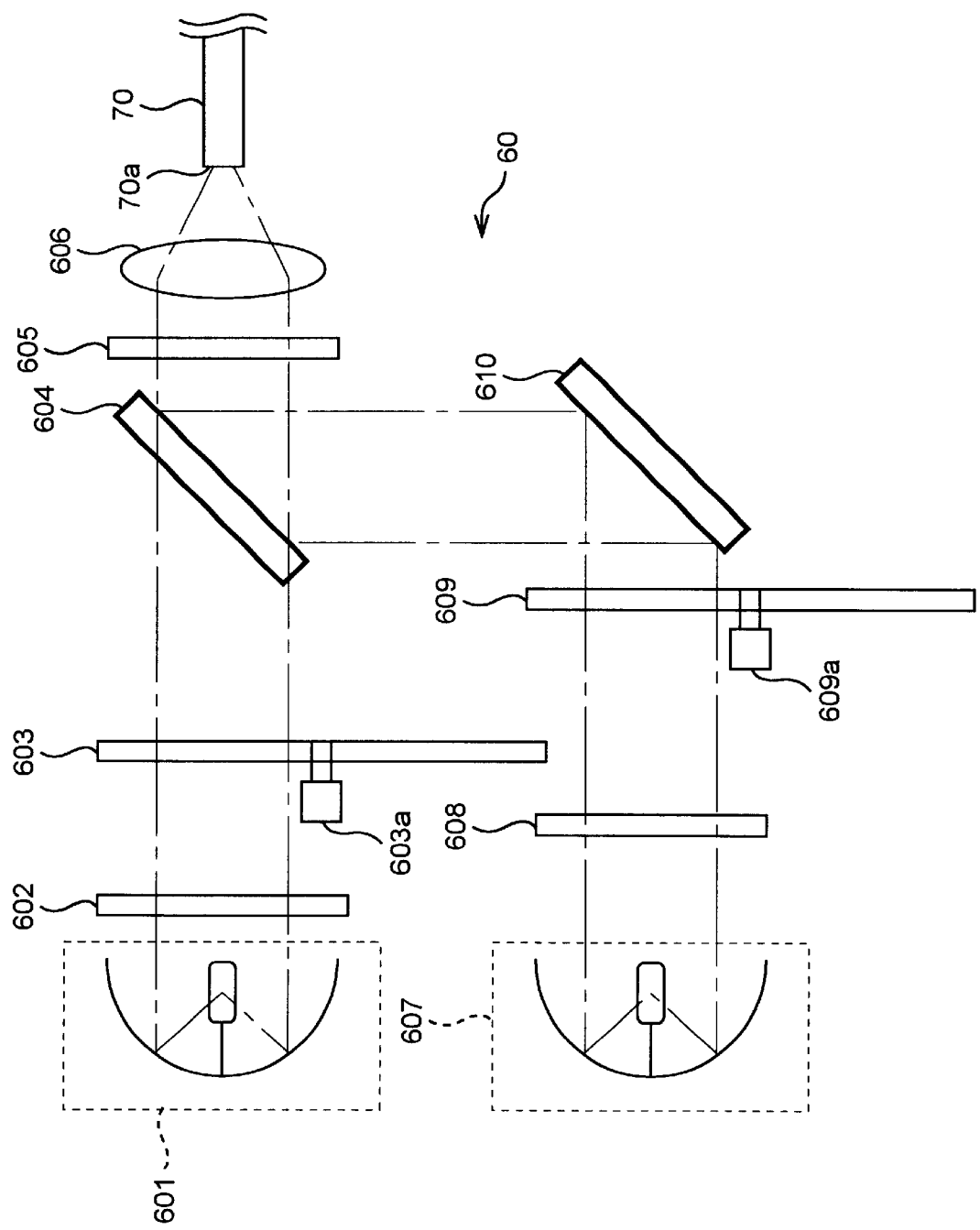
Figure 8A:
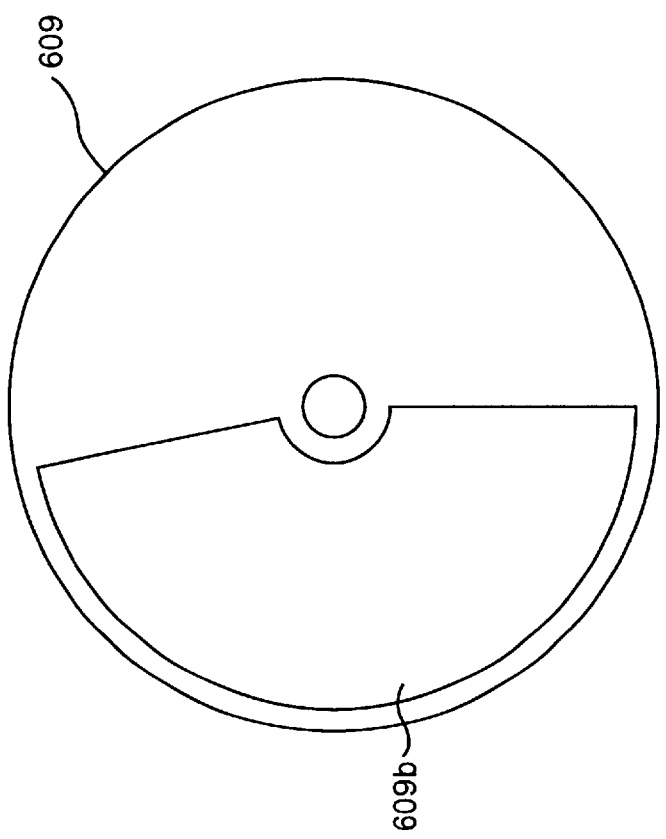
Figure 8B:
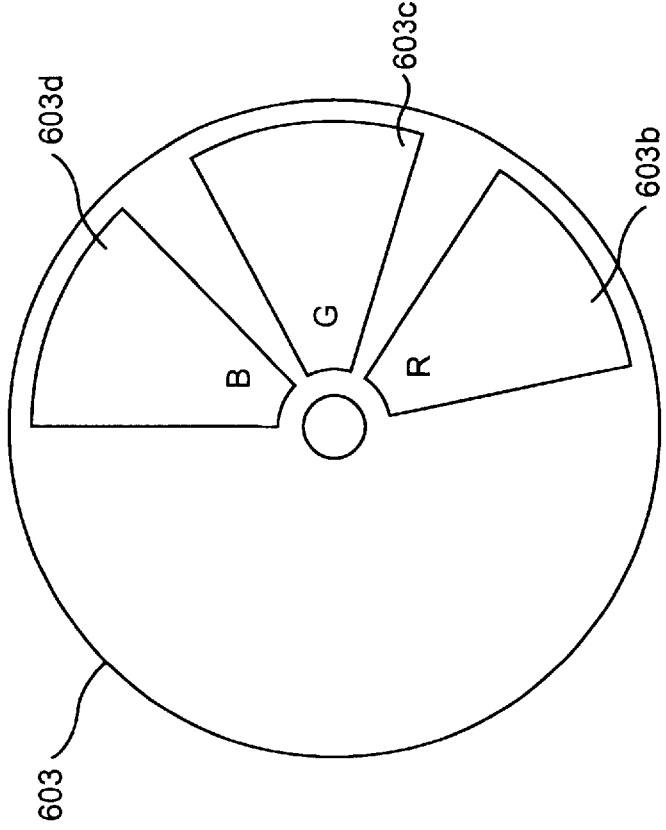

FIG. 5 is a view showing the arrangement of UV reflection filter 24, the infrared cut-off filter 23, and the UV transmission filters 29a, 29b. FIG. 6 is a graph showing the spectral reflectance characteristics of the UV reflection filter 24 when the beam is incident on the UV reflection filter 24 at an angle of 45 degrees. As shown in FIG. 5, on one face of the UV reflection filter 24, an antireflection coating 24a that allows white light to pass therethrough without causing loss is evaporated. On the other face thereof, a UV reflection coating 24b that reflects ultraviolet light is evaporated. When the beam is incident on this UV reflection filter 24 at an incident angle of 45 degrees, as shown in the graph in FIG. 6, light in the wavelength region not greater than approximately 400 nm is reflected at a reflectance of 80 percent or better (in the figure, reflectance is about 89 percent). At the same time, light in the wavelength region from approximately 400 nm to approximately 800 nm is reflected at a reflectance of about 4 percent. When the beam is incident on UV reflection filter 24 at the incident angle of 45 degrees, the beam solely consisting of wavelength components in the ultraviolet region is almost reflected without loss in the amount of light, whereas a beam solely consisting of wavelength components in the visible region is reflected at an extremely low rate of reflectance and almost transmitted through the filter 24. For incident light at an incident angle of 45 degrees, this UV reflection filter 24 exhibits high reflectance if the wavelength band of the beam is in the ultraviolet region, and high transmission if the wavelength band of the beam lies in the visible region. On the other hand, for any incident light at an incident angle other than 45 degrees, the UV reflection filter 24 does not exhibit such high reflectance or high transmission. For this reason, in the light source device 20 of the video endoscope system 1 according to this embodiment, as shown in FIG. 5, UV reflection filter 24 is inclined at an angle of 45 degrees to the collimated light beam consisting of red, green or blue wavelengths that serves as the illuminating light, and is also inclined to the collimated ultraviolet light beam at an angle of 45 degrees that serves as the excitation light.

Note that before entering the UV reflection filter 24, the wavelength components in the visible region are removed from the collimated ultraviolet light by the UV transmission filters 29a and 29b. This is done because the beam emitted from ultraviolet lamp 27a of the ultraviolet light source 27 includes some quantity of wavelength components in the visible region, and as shown in the graph of FIG. 6, the UV reflection filter 24 also exhibits some reflectance to beams consisting of wavelengths in the visible region. The UV transmission filters 29a and 29b of the two-filter configuration are used because UV transmission filters of a single-filter configuration might leave the wavelength components in the visible region. On the other hand, wavelength components in the infrared region are removed from the collimated visible light beams by the infrared cut-off filter 23 before entering the UV reflection filter 24. This is done because CCD the 14 built into the video endoscope 10 has a high sensitivity over a wide wavelength region, particularly to beams consisting of wavelengths in the infrared region.

Since the light source device in this embodiment is configured as described above, an optical system that combines the optical path of the collimated visible light beams and the optical path of the collimated ultraviolet light beam can be constituted with a single UV reflection filter 24. Therefore, the number of the optical elements of the whole of the optical system is small. Further, the optical axes of the optical system can be adjusted quickly and easily. In addition, since UV reflection filter 24 of which opposite faces are applied with the antireflection coating 24a and the UV reflection coating 24b respectively, is arranged at an angle of 45 degrees to both the collimated visible light beam and the collimated ultraviolet light beam, the collimated visible light beam can be transmitted efficiently through the filter 24, while the collimated ultraviolet light beam is efficiently reflected by the filter 24.

As described above, within an optical system of the light source device according to the present invention, a reduced number of optical elements can be achieved for the intended function, allowing easier and faster adjustment of the optical axes.

What is claimed is:

1. An optical system for a light source device which supplies both visible light to illuminate a subject and ultraviolet light to excite the subject to cause autoflorescence to a proximal end face of a light guide of a video endoscope, said video endoscope having the light guide for guiding the light to the subject, an objective optical system for forming an image of said subject, and an image pickup device for picking up said image, said optical system comprising:

a condenser lens for converging a light beam onto the proximal end face of said light guide;

a visible light source that emits a first collimated light beam having wavelengths in a visible region and is arranged so that said first collimated light beam enters said condenser lens;

an ultraviolet light source that emits a second collimated light beam having a wavelength in an ultraviolet region and is arranged so that said second collimated light beam orthogonally intersects said first collimated light beam; and a UV reflection filter arranged at an angle of 45 degrees to both said first collimated light beam and said second collimated light beam at a position where the first and second collimated light beams intersect, said UV reflection filter transmitting said first collimated light beam, while reflecting said second collimated light beam toward said condenser lens.

2. An optical system for a light source device according to claim 1, wherein said UV reflection filter is a transparent plate applied with a UV reflection coating for reflecting ultraviolet light on one face.

3. An optical system for a light source device according to claim 2, wherein said UV reflection coating is formed on a face of the UV reflection filter facing the ultraviolet light source.

4. An optical system for a light source device according to claim 1, wherein said UV reflection filter is a transparent plate applied with a UV reflection coating for reflecting ultraviolet light on one face and an antireflection coating transmitting visible light on the other face.

5. An optical system for a light source device according to claim 1, wherein said visible light source is a white light source that emits the first collimated beam of white light toward said condenser lens, and further comprising:

an R filter transmitting only red component in said first collimated light beam;

a G filter transmitting only green component in said first collimated light beam;

a B filter transmitting only blue component in said first collimated light beam;

an RGB rotating shutter arranged between said white light source and said UV reflection filter and rotating to repeatedly and sequentially insert said R filter, said G filter, and said B filter into an optical path of said first collimated light beam;

a UV rotating shutter arranged between said ultraviolet light source and said UV reflection filter, and rotating to intermittently intercept said second collimated light beam; and a control device that drives said RGB rotating shutter and said UV rotating shutter in synchronization with each other regarding their speeds and phases, so that a light beam consisting of a red component, a light beam consisting of a green component, a light beam consisting of a blue component, and a light beam having wavelengths in the ultraviolet region enter the proximal end face of said light guide in sequence.

6. An optical system for a light source device according to claim 5, further comprising:
   an infrared cut-off filter arranged between said visible light source and said UV reflection filter to remove components in the infrared region from the said first collimated light beam; and
   a UV transmission filter arranged between said ultraviolet light sources and said UV reflection filter, to transmit only components in the ultraviolet region in said second collimated light beam.

7. An optical system for a light source device according to claim 5, wherein said visible light source has a xenon lamp for emitting white light and a reflector for reflecting the white light emitted from said xenon lamp, so that the white light is converted into a collimated light beam, and
   said ultraviolet light source has an ultraviolet lamp for emitting ultraviolet light and a reflector for reflecting the ultraviolet light emitted from the ultraviolet lamp so that the ultraviolet light is converted into a collimated light beam.

8. An optical system for a light source device according to claim 1, further comprising
   a light aperture diaphragm arranged between said UV reflection filter and said condenser lens to adjust amount of light of said collimated light beams.

* * * * *